United States Patent
Meunier et al.

(10) Patent No.: US 11,268,968 B2
(45) Date of Patent: Mar. 8, 2022

(54) SOLUTION FOR DISSOCIATING VITAMIN D FROM VITAMIN-D BINDING PROTEIN, ASSOCIATED DETECTION METHOD AND USE

(71) Applicant: BIOMERIEUX, Marcy-L'Etoile (FR)

(72) Inventors: Valerie Meunier, La Tour de Salvagny (FR); Emmanuel Moreau, La Tour de Salvagny (FR)

(73) Assignee: BIOMERIEUX, Larcy-l'Etoile (FR)

( * ) Notice: Subject to any disclaimer, the term of this patent is extended or adjusted under 35 U.S.C. 154(b) by 58 days.

(21) Appl. No.: 16/240,904

(22) Filed: Jan. 7, 2019

(65) Prior Publication Data

US 2019/0137524 A1 May 9, 2019

Related U.S. Application Data

(62) Division of application No. 14/915,325, filed as application No. PCT/FR2014/052296 on Sep. 16, 2014, now Pat. No. 10,222,389.

(30) Foreign Application Priority Data

Sep. 17, 2013 (FR) ..................... 13 58940

(51) Int. Cl.
*G01N 33/82* (2006.01)
(52) U.S. Cl.
CPC .................. *G01N 33/82* (2013.01)
(58) Field of Classification Search
CPC .......... G01N 33/82; G01N 33/53; C08K 5/09; C07C 17/361; C07C 19/08
See application file for complete search history.

(56) References Cited

U.S. PATENT DOCUMENTS

| 4,822,860 A | 4/1989 | Sekiya |
| 5,648,325 A | 7/1997 | Kitamura et al. |
| 2005/0209468 A1 | 9/2005 | Burns |
| 2014/0147935 A1 | 5/2014 | Imus et al. |

FOREIGN PATENT DOCUMENTS

| CN | 101328216 | 12/2008 |
| CN | 101413944 | 4/2009 |
| GB | 2 166 153 | 4/1986 |
| JP | 57-176536 | 10/1982 |
| JP | 2002-097230 | 4/2002 |
| WO | 99/67211 | 12/1999 |
| WO | 2007/039194 | 4/2007 |
| WO | 2011/122948 | 10/2011 |
| WO | 2012/091569 | 7/2012 |
| WO | 2012/136720 | 10/2012 |

OTHER PUBLICATIONS

Mary Bedner et al., "Development and . . . human serum", Journal of Chromatography, vol. 1240, Mar. 28, 2012, pp. 132-139.
Kucukkolbashi et al., Simultaneous and accurate determination of water and fat-soluble vitamins in multivitamin tablets by using an RP-HPLC method. Quim. Nova, 2013, vol. 36, No. 7, pp. 1044-1051.
Stadalius et al., "A method for the low-level . . . tandem mass spectrometry", Journal of Chromatography A., 1123 (2006) 10-14.
Wojcik et al., "Separation of perfluorocarboxylic . . . electrophoresis with UV detection", Electrophoresis 2005, 26, 1080-1088.
F. Xiao et al., "Effects of Monovalent Cations . . . Experimental Studies and Modeling", Edviron. Sci. Technol., 2011, 45, pp. 10028-010035.
S. Ji et al., "LC-MS/MSDeterminatlon of 7 Bio-amines in the Grape", Chemical vol. 2013, 49 (6), pp. 697-700.
Shuzo Kutsuna et al., "Preferential solvation of . . . Yasuda-Shedlovsky plot", Atmospheric Environment 49, 2012, 411-414.

*Primary Examiner* — Shafiqul Haq
(74) *Attorney, Agent, or Firm* — Clark & Brody LP

(57) ABSTRACT

A buffer solution includes methanol and the at least one fluoroalkyl surfactant selected from perfluorocarboxylic acids, perfluorosulfonic acids and their salts. A method for detecting and quantifying, in vitro, vitamin D and/or at least one vitamin D metabolite in a biological sample includes treating the sample by incorporating at least one fluoroalkyl surfactant and methanol so as to dissociate the vitamin D and/or its metabolite(s) to be detected from vitamin D binding protein; and detecting and quantifying vitamin D and/or at least one of its metabolites, in particular by immunoassay. A kit for detecting and quantifying vitamin D and/or at least one vitamin D metabolite by immunoassay and including the solution is provided.

15 Claims, 1 Drawing Sheet

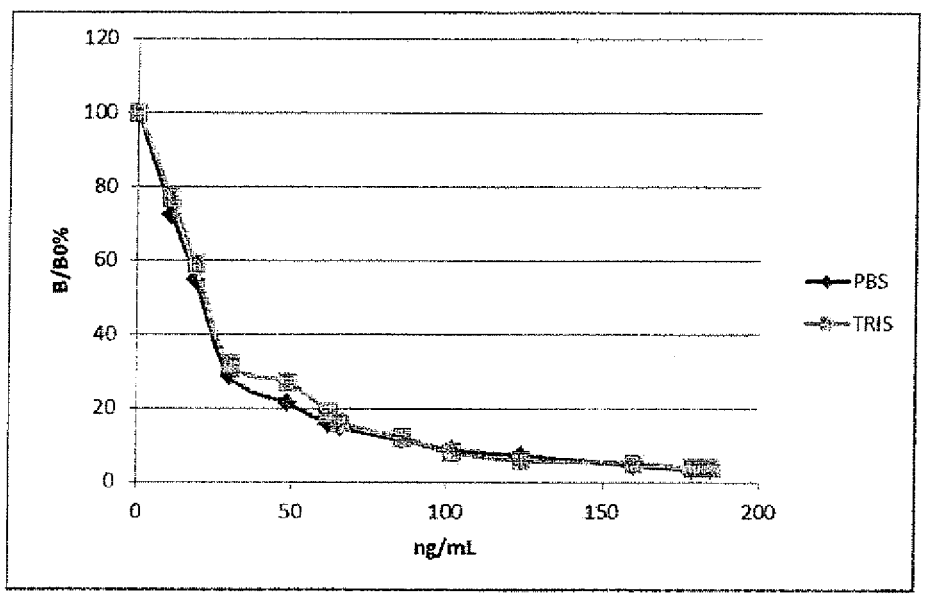

SOLUTION FOR DISSOCIATING VITAMIN D FROM VITAMIN-D BINDING PROTEIN, ASSOCIATED DETECTION METHOD AND USE

This application is a Divisional of U.S. Ser. No. 14/915,325 filed on Feb. 29, 2016, which is a national phase of PCT/FR2014/052296 filed on Sep. 16, 2014.

FIELD OF INVENTION

The present invention relates to the technical field of detecting vitamin D. More particularly, the invention provides the use of an association of a fluoalkyl surfactant and an alcohol for releasing vitamin D and/or one of its metabolites from the Vitamin D binding protein, a solution containing such an association, an in vitro method of detecting/quantifying vitamin D and/or at least one metabolite of vitamin D using such an association, and a kit for detecting/quantifying by immunoassay making use of such an association.

BACKGROUND ART

Vitamin D is an important substance having numerous implications in the biological processes of the human and animal body. Biologically active vitamin D is known to regulate, amongst other things, the fixing of calcium from the intestine, and bone mineralization, and it has an influence on many other metabolic pathways, such as for example the insulin system. A deficiency or an excess of vitamin D can have various consequences. In particular, it is known that vitamin D deficiency leads to severe illnesses such as osteoporosis and rickets.

Furthermore, excess vitamin D, in particular due to an overdose, is toxic. In particular, a high level of vitamin D can lead to hypercalcemia caused by an increase in the absorption of calcium by the intestine. Other toxic effects of vitamin D are manifested by an increase in blood pressure, gastrointestinal troubles such as anorexia, nausea, often followed by excessive production of urine, polydipsia, fatigue, nervousness, itching, or indeed kidney failure.

As mentioned in application WO 2012/091569, it has also been discovered in recent years that vitamin D modulates the immune system and reduces inflammation. It has also been suggested that vitamin D can prevent cancers of the colon, the ovaries, and the breast.

Consequently, it is important to be able to measure or quantify vitamin D, i.e. to determine its concentration, so as to reveal any potential deficiencies or excesses.

Vitamin D is present in the organism in two forms, namely vitamin $D_2$ (ergocaliferol) and vitamin $D_3$ (cholecalciferol) of formulae that are set out below (in which the positions in the vitamin D are numbered in compliance with steroid nomenclature).

Vitamine $D_2$ (ergocalciferol):

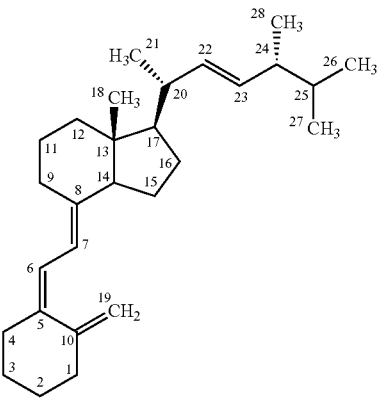

Vitamine $D_3$ (cholecalciferol):

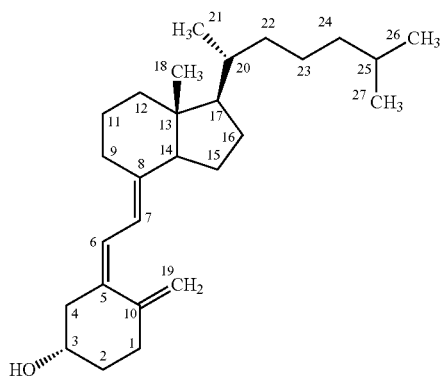

Vitamin $D_2$ is the exogenous form of vitamin D, coming from food. Vitamin $D_3$ is the endogenous form of vitamin D as produced by the organism under the action of ultraviolet rays from sunlight on the skin. The vitamin $D_3$ that is produced by the skin binds with the vitamin D binding protein, which transports it to the liver. Both forms may also come from nutritional supplements. Various metabolites of vitamin D are produced. In particular, two-step metabolization takes place, the first step consisting in producing 25-hydroxy vitamin D ($D_2$ or $D_3$), followed by producing 1,25-dihydroxy vitamin D ($D_2$ or $D_3$).

Measuring the quantity of vitamin D itself is of limited interest, given that its concentration fluctuates strongly as a function of diet. The same applies to 1,25-dihdyroxy vitamin D metabolites which are present in fairly low concentration and which also fluctuate.

The circulating forms of vitamin D are essentially metabolites of the 25-hydroxy vitamin D type. Thus, the preferred mode for obtaining information about the overall concentration of vitamin D in a patient is assaying 25-hydroxy vitamin D.

The bonding of 25-hydroxy vitamin D, or more generally of vitamin D and its metabolites, to the vitamin D binding protein (DBP) complicates assaying its components. In order to obtain an adequate assay, it is necessary to release the hapten to be assayed from the DBP by causing them to dissociate. Thus, various solutions have been proposed for obtaining the release of vitamin D and its metabolites after dissociating DBP and before detecting them.

Various techniques listed in patent application WO 2007/039194 and in patent application WO 2012/091569 have been developed. Only some of them are listed below.

An old technique, used in particular in application WO 99/67211 consists in preparing a sample of plasma or serum in order to determine vitamin D by ethanol precipitation. The precipitates are then eliminated in order to recover the ethanolic supernatent containing the soluble metabolites of vitamin D. Precipitation by means of alcohol or another organic solvent such as acetonitrile has commonly been used in the past. Nevertheless, that technique cannot be automated and requires numerous manual operations (adding solvents to the serum, mixing, centrifuging, recovering the organic phase, drying on a column or otherwise, re-suspension in a liquid solvent), thus making it obsolete these days because of the high degree of variation that is observed between operators.

Patent application WO 2007/039194 proposes using a solution containing 5% to 30% by volume of one or more amphiphilic reagents selected from dimethylsulfoxide (DMSO) and liquid organic amides, and optionally 0.7% to 8% by volume of a short chain alcohol ($C_1$-$C_3$). The amphiphilic compounds used in that document are substances that are toxic, or indeed dangerous if it is DMSO.

Patent applications WO 2011/122948 and WO 2012/091569 in the name of Future Diagnostics describe immunoassay and an agent that enable vitamin D to be released from its binding protein and that uses a fluoroalkyl surfactant. The Applicant has made use of that solution, but has nevertheless found that the dissociation that is obtained is still not sufficient.

SUMMARY OF THE INVENTION

The object of the invention is to propose a more effective dissociation technique that is easy to perform and that leads to effective release of vitamin D and its metabolites, after dissociating the vitamin D binding protein (DBP), subsequently enabling them to be detected and quantified adequately.

In the context of the present invention, the object is to provide a new solution for dissociating vitamin D or one of its metabolites from vitamin D binding protein (DBP), that is more effective than the techniques proposed in the prior art by Future Diagnostics in its patent applications WO 2011/122948 and WO 2012/091569. In addition, the solution described in the present invention does not present the toxicity problems of the solutions as proposed in particular in patent application WO 2007/039194.

In this context, the invention provides the use of at least one fluoroalkyl surfactant, and in particular a perfluoroalkyl surfactant, and of at least one alcohol having 1 to 4 carbon atoms for dissociating vitamin D and/or a vitamin D metabolite from vitamin D binding protein. Such joint use makes it possible to increase significantly the dissociation rate of vitamin D or one of its metabolites from vitamin D binding protein, in comparison with a similar use differing solely by the absence of alcohol. In the use of the invention, the fluoroalkyl surfactant, and in particular the perfluoroalkyl surfactant, and the alcohol having 1 to 4 carbon atoms are incorporated in a liquid sample including the vitamin D and/or a vitamin D metabolite (referred to as an analyte or vitamin D analyte), associated with vitamin D binding protein. The analyte for dissociation is thus in contact both with the fluoroalkyl surfactant and with the alcohol, which, when used together, enable dissociation to be achieved that is greater than when using the same fluoroalkyl surfactant on its own. The joint use of fluoroalkyl surfactant, and in particular perfluoroalkyl surfactant, and alcohol having 1 to 4 carbon atoms, leads to effective dissociation between vitamin D binding protein and vitamin D and/or one of its metabolites.

In particular, the fluoroalkyl surfactant and the alcohol are used in quantities such that the ratio multiplied by 100 of the weight of surfactant, when it is solid, or of the volume of surfactant, when it is liquid, over the volume of alcohol lies in the range 10% to 60%, preferably in the range 15% to 40%, and more preferably in the range 15% to 30%. The solid or liquid nature is assessed at ambient temperature (in particular at 22° C.) and at atmospheric pressure (in particular at 1013 hectopascals (hPa)).

Advantageously, the fluoroalkyl surfactant is selected from perfluorocarboxylic acids, perfluorosulfonic acids and their salts, and in particular from perfluorohexanoic acid, perfluoroheptanoic acid, and perfluorooctanoic acid, and their salts. Perfluorohexanoic acid is also known as perfluorocaproic acid or indeed as undecafluorohexaonic acid; its chemical abstract service (CAS) registration number is 307-24-4. Perfluorooctanoic acid is also known as perfluorocaprylic acid or indeed as pentadecafluorooctanoic acid; its CAS number is 335-67-1. In general, the salts of these perfluoroalkyl acids are solid, whereas the corresponding free acids are liquid.

Perfluorohexanoic acid, possibly in salt form, is the preferred fluoroalkyl surfactant, since it presents better degradability compared with longer chain fluoroalkyl surfactants.

In preferred manner, the alcohol used has 1 to 3 carbon atoms and is selected from methanol, ethanol, n-propanol, and isopropanol. Methanol is the preferred alcohol in the invention since it makes it possible to obtain performance that is better in terms of the reproducibility of the results of the assaying performed after dissociation, and provides a good compromise in terms of improving dissociation and the reproducibility of the results obtained.

In particularly advantageous manner, the dissociation is performed with perfluorohexanoic acid and methanol.

In the context of the invention, the dissociation may be performed in the presence of an additional surfactant selected, in particular from block copolymers based on ethylene oxide and propylene oxide, polysorbates, and polyethylene glycol ethers.

By way of example, the invention is performed to dissociate 25-hydroxy vitamin D, and in particular 25-hydroxy vitamin $D_2$ and/or 25-hydroxy vitamin $D_3$ from vitamin D binding protein.

The alcohol and the fluoroalkyl surfactant may be incorporated separately in the sample in which it is desired to obtain dissociation, or they may be incorporated simultaneously. Under such circumstances, a single solution is used referred to as a "dissociation" solution, in order to minimize manipulations.

The invention also provides such solutions comprising at least one fluoroalkyl surfactant, and in particular a perfluoroalkyl surfactant, and at least one alcohol having 1 to 4 carbon atoms.

Such solutions may be said to be aqueous and they include a large quantity of water, which generally represents more than 80% by volume relative to the total volume of the solution.

Advantageously, such a solution comprises a percentage of fluoroalkyl surfactant expressed by volume when the surfactant is liquid, or by weight when it is solid, relative to the total volume of the solution lying in the range 0.1% to 3%, preferably in the range 1% to 2%. In equally preferred manner, such a solution comprises a percentage by volume of alcohol relative to the total volume of the solution lying in the range 0.5% to 10%, and preferably in the range 2% to 7%.

The same preferences concerning the choice of the alcohol and of the fluoroalkyl surfactant and their relative quantities, stated with reference to the use, apply to the dissociation solutions of the invention.

In an advantageous variant, the dissociation solutions of the invention also contain another surfactant selected from block copolymers based on oxide ethylene oxide and propylene oxide, polysorbates, and polyethylene glycol ethers. Without seeking to be tied to any particular interpretation of the results, such an additional surfactant can improve the solubility of vitamin D or of its metabolite that is to be assayed. The use of such an additional surfactant, such as Pluronic® F-127, which is a polyol corresponding to a block copolymer based on oxide ethylene oxide and propylene oxide serves in particular to improve the reproducibility of the results. It is found that the final assay is more reliable. By way of non-limiting example, it is possible to use Pluronic® F-127 at a concentration in the dissociation solution that preferably lies in the range 0.1% to 3% (by volume relative to the final volume of the dissociation solution).

In general, the dissociation solutions of the invention are buffered, in particular to a pH lying in the range 6 to 8.

The buffers conventionally used in the field of diagnosis may be incorporated in the solution, so as to obtain a pH in the desired range and so as to stabilize it. By way of example, a phosphate-buffered saline (PBS) buffer or a tris buffer (tris-hydroxymethyl aminomethane) may be used.

A base may be incorporated in order to adjust the pH. Such a base may be any base that is conventionally used for this purpose, such as KOH, NaOH, LiOH, or $Na_2HPO_4$.

Such a dissociation solution may be prepared by mixing a buffer of concentration that preferably lies in the range 1 millimole (mM) to 500 mM, a fluoroalkyl surfactant of concentration that preferably lies in the range 0.1% to 3% (by weight or by volume, depending on the solid or liquid nature of the surfactant, relative to the final volume of the dissociation solution) and an alcohol of concentration that preferably lies in the range 0.5% to 10% (by volume relative to the final volume of the dissociation solution) in demineralized water. The pH of the dissociation solution is adjusted depending on the selected buffer, by adding acid or by adding base so as to obtain a value lying in the range 4 to 8, and preferably around 7. When the dissociation solution contains an additional surfactant, it may be introduced at any stage.

Advantageously, such dissociation solutions do not contain any of the following compounds: dimethyl sulfoxide, dimethylformamide, N,N-dimethylacetamide, tetramethylurea, N-methylpyrrolidone, 1,3-dimethyl-3,4,5,6-tetrahydro-2(1H)-pyrimidone, triamide hexamethyl phosphoric acid.

The invention also provides a detection and quantification method for detecting and quantifying, in vitro, vitamin D and/or at least one vitamin D metabolite in a biological sample, the method comprising the following steps:

a) a step of treating the sample by incorporating at least one fluoroalkyl surfactant and at least one alcohol having 1 to 4 carbon atoms, so as to dissociate including at least one fluoroalkyl surfactant and at least one alcohol having 1 to 4 carbon atoms from vitamin D binding protein; and b) a step of detecting and quantifying vitamin D and/or at least one of its metabolites.

The dissociation step a) should be performed before detection and quantification step b).

Advantageously, in such a detection and quantification method, the treatment of step a) is performed by mixing the sample with a dissociation solution of the invention. Usually, 1 to 20 volumes of dissociation solution, preferably 5 to 10 volumes, more preferably 6 to 8 volumes, and in particular about 7 volumes of solution are used for 1 volume of sample. The selected volume is a function of the presumed concentration of vitamin D and/or vitamin D metabolite that is to be detected (referred to as analyte to be detected).

Advantageously, the detection and quantification method of the invention is performed on a sample of blood, of serum, or of plasma.

The detection and quantification method is suitable in particular for detecting and quantifying 25-hydroxy vitamin $D_2$ and/or 25-hydroxy vitamin $D_3$.

In step b), detection and quantification are preferably performed by performing an immunoassay, or indeed by mass spectrometry.

The invention also provides a kit for detecting and quantifying vitamin D and/or at least one vitamin D metabolite by immunoassay and comprising a dissociation solution of the invention. Such a kit may also include a binding partner for vitamin D or one of its metabolites and/or a solid phase on which a hapten analogous to vitamin D and/or the vitamin D metabolite(s) for detection is bonded, which hapten is recognized by the marked antibody.

BRIEF DESCRIPTION OF THE DRAWINGS

The sole Figure plots a B/B0% ratio obtained over an ng/mL range of analyte for two different buffers.

DETAILED DESCRIPTION OF THE INVENTION

In the context of the invention, vitamin D metabolites cover all compounds that contain the skeleton of vitamin $D_2$ or the skeleton of vitamin $D_3$, and in particular:

25-hydroxy vitamin D, which specifies the metabolites of vitamin D that are hydroxylated in position 25, i.e. 25-hydroxy vitamin $D_2$ and 25-hydroxy vitamin $D_3$; and the 1,25 and 24,25-dihydroxy vitamin D forms, which specify the metabolites of vitamin D that are dihydroxylated, respectively in positions 1 and 25 or in positions 24 and 25.

In the methods of uses of the invention, dissociation may be performed by incorporating, in the sample for analysis, both the fluoroalkyl surfactant and also the $C_1$-$C_4$ alcohol and preferably $C_1$-$C_3$ alcohol that have been selected, either together or separately. After such incorporation, no separation is needed, and detection can be performed directly on the resulting sample. Preferably, in order to limit manipulations, a previously prepared solution containing the fluoroalkyl surfactant and the $C_1$-$C_4$ alcohol and preferably $C_1$-$C_3$ alcohol that have been selected is incorporated in the sample, and in particular a solution in accordance with the invention.

In order to enhance dissociation, the sample containing the fluoroalkyl surfactant and in particular the perfluoroalkyl surfactant and $C_1$-$C_4$ alcohol and preferably $C_1$-$C_3$ alcohol that have been selected is subjected to mixing. Such mixing may be performed with any appropriate device, and in particular by means of a reaction cone acting as a pipette, as in the Applicant's Vidas® technology (Vidas® Manuel Instrument, 2005, Chapitre 2 Description fonctionnelle, 2-1 to 2-16, bioMérieux France [Vidas® Instrument manual, 2005, Chapter 2, Functional description, 2-1 to 2-16, bioMérieux France]).

The vitamin D or one of its metabolites may be detected using any technique known to the person skilled in the art, and in particular by performing a test using a binding partner of the analyte to be detected, and in particular an immunological test (also known as an immunoassay test), or indeed by mass spectrometry.

Naturally, the prefix "immuno" in the term "immunoassay", for example, should not be considered in the present application as indicating strictly that the binding partner is necessarily a partner of immunological origin, such as an antibody or an antibody fragment. As is well known to the person skilled in the art, this term is used more widely to designate tests and methods in which the binding partner is not solely a partner of immunological origin and/or nature, but may consist, for example, of a receiver for the analyte that is to be detected and/or quantified, the condition being that the binding partner in question must be capable of binding to the looked-for analyte, and preferably in specific manner. Thus, it is known to use the term "enzyme-linked immunoabsorbant assay (Elisa)" for assays that make use of binding partners that are not strictly speaking immunological, and that are referred to more broadly as "ligand binding" assays, even though the team "immuno" is included in the acronym Elisa. For the purposes of clarity and uniformity, the term "immuno" is used in the present application to cover any biological analysis using at least one binding partner suitable for binding with the looked-for analyte and for detecting and/or quantifying it, preferably in specific manner, even when said binding partner is not strictly speaking of immunological nature or origin.

The immunological test is preferably competition assaying, which is a form of assaying well known to the person skilled in the art and which is used when the analyte is a hapten. It consists in assaying the in-sample analyte, specifically vitamin D and/or at least one of its metabolites, by setting up competition between the analyte of the sample and an analog of the analyte. The immunological reaction is then revealed by the presence of a tracer.

The analyte analog may be used in the competition reaction without prior coupling or after coupling to a marker in order to form a conjugate or tracer.

Immunological assay by competition also requires the use of a binding partner of the analyte relative to which the analyte analog and the analyte enter into competition. When the analyte analog is not coupled to a marker (it is not the tracer but the capture partner), the binding partner is marked in order to constitute the reaction tracer. When the analyte analog is coupled to a marker (it is then the tracer), the binding partner then becomes the capture partner.

The measured signal as emitted by the tracer is then inversely proportional to the quantity of analyte in the sample.

The term "marker" is used to mean any molecule containing a group that reacts with the capture partner or the analyte analog, depending on the format, directly without chemical modification, or after chemical modification to include such a group, which molecule is capable of generating a detectable signal either directly or indirectly. Such a reactive group may in particular be a primary amine. A non-limiting list of such direct detection markers is as follows:

enzymes that produce a signal that is detectable, e.g. by colorimetry, fluorescence, luminescence, such as horse-radish peroxydase, alkaline phosphatase, β-galactosidase, and glucose-6-phosphate dehydrogenase;

chromophores such as fluorescent, luminescent, and dye compounds;

radioactive molecules such as $^{32}P$, $^{35}S$, or $^{125}I$;

fluorescent molecules such as Alexa or phycocyanines; and electrochemiluminescent salts such as organo-metallic derivatives based on acridinium or ruthenium.

Indirect detection systems may also be used, such as for example ligands capable of reacting with an anti-ligand. The ligand then corresponds to the marker for acting with the analyte analog or the binding partner to constitute the tracer.

Ligand/anti-ligand pairs are well known to the person skilled in the art as applies for example to the following pairs: biotin/streptavidin, hapten/antibody, antigen/antibody, peptide/antibody, sugar/lectin, polynucleotide/polynucleotide complement.

The anti-ligand can then be detected directly by the above-described direct detection markers or may itself be detectable by using some other ligand/anti-ligand pair, and so on.

Under certain conditions, these indirect detection systems can lead to the signal being amplified. This signal amplification technique is well known to the person skilled in the art, and reference may be made to prior patent applications FR 2 781 802 or WO 95/08000 in the name of the Applicant.

Depending on the type of marker used, the person skilled in the art adds reagents enabling the marking to be viewed or a signal to be emitted that is detectable by any appropriate type of measuring apparatus, such as for example: a spectrophotometer; a spectrofluorometer; or indeed a high definition camera.

The term "binding partner" for vitamin D or one of its metabolites, or indeed for a plurality of these compounds, is used to mean any molecule capable of binding with vitamin D or one of its metabolites, or indeed with several of these compounds (referred to in general manner as "vitamin D analytes"). As an example of a vitamin D analyte binding partner, mention may be made of antibodies, antibody fractions, nanofitins, vitamin D analyte receivers, or any other protein that is known to interact with vitamin D analyte.

By way of example, the binding partner antibodies may be either polyclonal antibodies or monoclonal antibodies.

Polyclonal antibodies may be obtained by immunizing an animal with the target vitamin D analyte as the immunogen, followed by recovering the looked-for antibodies in purified form by taking serum from said animal, and separating said antibodies from the other constituents of the serum, in particular by affinity chromatography on a column having fixed thereon an antigen that is specifically recognized by the antibodies, in particular the immunogen.

Monoclonal antibodies may be obtained by the hybridoma technique that is well known to the person skilled in the art. Monoclonal antibodies may also be recombinant antibodies obtained by genetic engineering, using techniques well known to the person skilled in the art.

As examples of antibody fragments, mention may be made of Fab, Fab', F(ab')2 fragments and of single chain variable fragments (scFv) and double-stranded variable fragments (dsFv). These functional fragments may be obtained in particular by genetic engineering.

Nanofitins (trade name) are small proteins that, like antibodies, are capable of binding to a biological target, thus making it possible to detect it, capture it, or merely to target it within an organism.

The binding partners used may be specific or non-specific to the vitamin D analyte. They are said to be "specific" when they are capable of binding in exclusive or almost exclusive manner with the vitamin D analyte. They are said to be "non-specific" when the selectivity of the binding with the vitamin D analyte is weak so they are also capable of binding with other ligands, such as other proteins or antibodies. In a preferred implementation, specific binding partners are preferred.

Anti-vitamin D analyte antibodies are known, and they are described in particular in Hollis, Clin. Chem. 31/11, 1815-1819 (1985) and Holis, Clin. Chem. 39/3, 529-533 (1993) and in patent EP 1 931 711. They may also be obtained from various suppliers such as Bioventix (UK).

Binding partners or vitamin D analogs, when they are used in capture, may optionally be bound to a medium, such as microtitration plates, latexes, reaction cones, beads having a diameter of the order of one hundred micrometers to a nanometer, using any technique well known to the person skilled in the art. The vitamin D analogues are preferably immobilized on a solid phase.

It is possible in particular to make use of a medium that has been functionalized with avidin and/or streptavidin and to bind on the solid phase a biotinylated analyte analog. Functionalization techniques are well known to the person skilled in the art who can make reference thereto.

In conventional manner, in order to determine the quantity of vitamin D and/or of at least one of its metabolites, the signal, which is inversely proportional to the quantity of analyte in the sample, may be compared with a calibration curve previously obtained using techniques that are well known to the person skilled in the art. Thus, by way of example, the calibration curve may be obtained by performing an immunological assay using the same binding partner together with increasing known quantities of vitamin D. A curve is thus obtained with concentration of vitamin D plotted along the abscissa axis and the corresponding signal obtained after immunological assay plotted up the ordinate axis.

The detection/quantification method of the invention may be applied directly to the format of commercial tests available for detecting/quantifying vitamin D. Such formats for assaying vitamin D and/or one of its metabolites are sold in particular by Abbott (Architect 25-OH vitamin D, ref. 3L52), DiaSorin (Liaison® 25-OH vitamin D total assay, ref. 310600), IDS (IDS-iSYS 25-hydroxy vitamin D assay, ref. IS-2700), Siemens (Advia Centaur® vitamin D total, ref. 10491994), Roche (Elecys vitamin D total).

In conventional manner, performing an immunoassay thus requires the reagents necessary for immunological detection as described above, which reagents are to be incorporated in the sample. Advantageously, the dissociation and thus the incorporation in the sample for study, both of the fluoroalkyl surfactant and of the $C_1$-$C_4$ alcohol, preferably a $C_1$-$C_3$ alcohol, that have been selected, are performed before incorporating such reagents.

It is also possible to use mass spectrometry for performing the detection/quantification step once the dissociation has been obtained. This technique is an analysis technique that makes it possible to determine the molar masses of the compounds being analyzed, and also enables their molecular structure to be identified, and even enables them to be quantified. When applied to a complex mixture such as a biological fluid, it needs to be coupled to a separation technique that enables the complexity of the fluid to be reduced. Usually that comprises gas chromatography (GC) or liquid chromatography (LC). Tandem mass spectrometry (MS/MS) combines two analyzers and can be used for detection/quantification purposes. The ionic compounds selected in the first analyzer are analyzed more finely in the second. Such double analysis serves to increase significantly the specificity of the method. For this technique, reference may be made in particular to Van den Broek et al., J. Chromatogr. B 929 161-179 (2013).

The biological sample with which the method of the invention can be performed is any animal and preferably human biological sample that might contain the analyte (vitamin D or one of its metabolites), in which an immunoassay or a mass spectrometry analysis can be performed. Such samples are well known to the person skilled in the art. The sample used in the assay method may optionally be modified prior to being used. As examples of such samples that are not previously modified, mention may be made of biological fluids such as total blood, and as examples of samples that have been previously modified, also known as sample derivatives, mention may be made of serum, plasma, cells recovered from a biopsy, or from a surgery, and then cultured in vitro. The concentration of vitamin D or of one of its metabolites may then be assayed in the culture supernatent, or indeed in the cellular lysate.

The examples below serve to illustrate the invention, but they have no limiting character.

For each experimentally tested condition, the tables given in the examples give the relative fluorescence value (RFV) signal as determined by the Vidas® machine (bioMérieux). Often, a plurality of independent measurements were taken for each of the conditions. The "mean RFV" corresponds to the arithmetic mean of such independent measurements.

In order to verify the effectiveness of the dissociation solutions, the results obtained with two biological samples having different concentrations of 25-OH vitamin D were compared by calculating the % ratio between the two signals obtained (written $RFV_{No.2}/RFV_{No.1}$, sample No. 1 being the sample with the lower concentration of 25-OH vitamin D). For repeated independent measurements, the ratio was calculated from mean RFVs. The smaller this ratio, the better the dissociation.

The coefficient of variation (CV) is defined as the ratio between the standard deviation and the mean. It is often expressed as a percentage (CV %). The CV % is a measure of relative dispersion and it reflects the reproducibility of the results. A reduction in the value obtained is indicative of an improvement in reproducibility.

Some of the experiments described form part of experiment optimization plans that were constructed by using Tagushi tables. When the optimum is a nominal value, as for a reproducibility study (fixed signal value), variance around the value may be considered as being the result of noise factors, and thus as being detrimental to reproducibility. On the basis of repeated experimental data, the signal-to-noise ratio (S/N) may be calculated and it is defined using the formula $10 \times \log_{10}(\text{mean}^2/\text{standard deviation}^2)$. The S/N ratio, sometimes known as the Taguchi constant, is indicative of the reproducibility of the results. An increase in the value obtained is indicative of an improvement in reproducibility.

The ratio B/B0% is the signal obtained for the tested range point divided by the signal obtained for the range point having 0 nanograms per millimeter (ng/mL) of analyte, multiplied by 100.

In the various tables that follow, with the exception of Table 5, the perfluoroalkyl acids used were liquid, their percentages being given by volume relative to the total volume of the dissociation solution. For the alcohol used, in all cases, the percentages are given by volume relative to the total volume of the dissociation solution.

EXAMPLE 1—ADVANTAGE OF DISSOCIATION USING A METHANOL AND PERFLUOROHEXANOIC ACID MIXTURE COMPARED WITH PERFLUOROHEXANOIC ACID ALONE

Preparation of Dissociation Solutions

Comparative dissociation solution: the components for preparing the PBS buffer (5 mM of sodium hydrogen phosphate ($Na_2HPO_4$), 1.5 mM of potassium dihydrogen phosphate ($KH_2PO_4$), 131 mM of NaCl) and 0.75% perfluorohexanoic acid were dissolved in demineralized water by stirring for about 30 minutes (min). The pH was adjusted to 7.2 using 6N NaOH.

Solution of the invention: the components for preparing the PBS buffer (5 mM of sodium hydrogen phosphate ($Na_2HPO_4$), 1.5 mM of potassium dihydrogen phosphate ($KH_2PO_4$), 131 mM of NaCl), 0.75% perfluorohexanoic acid, and 5% of methanol were dissolved in demineralized water by stirring for about 30 min. The pH was adjusted to 7.2 using 6N NaOH.

Method of Quantifying Total 25-0H Vitamin D

Immunological assays were performed using a Vidas® immunoanalysis machine (from bioMérieux). The single-use cone serves both as the solid phase for the reaction and as a pipetting system. The cartridge was made up of ten wells covered in a sealed and labeled aluminum sheet. The first well had a cut-out portion to facilitate inserting the sample. The last well was an optical cuvette in which the fluorescence of the substrate was measured. The various reagents needed for analysis were contained in the intermediate wells. All of the steps of the test were performed automatically by the instrument. They were constituted by a succession of suck/blow cycles of the reaction medium.

a) Sensitizing and Passivating the Cone

The cones were sensitized with 300 microliters (μL) of a carrier anti-protein antibody solution diluted to 10 micrograms per milliliter (μg/mL) in a 50 mM MES buffer of pH 6.1. After 6 hours (h) of incubation at +18/25° C., washing was performed with a 9 grams per liter (g/L) solution of NaCl. Thereafter, there were added 300 μL of a solution of vitamin D coupled to the carrier protein and diluted to 150 nanograms per milliliter (ng/mL) in a 200 mM tris buffer of pH 6.2 containing human albumin. Sensitization/passivation continued at +18/25° C. overnight. The cones were emptied, dried, and then stored at +4° C. while sheltered from moisture until they were used.

b) Pretreatment of the Sample

The sample for assay (100 μL) was introduced into the first well of the cartridge. The sample and the pretreatment reagent (comparative dissociation solution or solution of the invention) were put together for separating the vitamin D contained in the sample from its binding protein. The Vidas® machine mixed 48 μL of sample with 340 μL of dissociation solution; the mixture was incubated at 37° C. for 5 min.

c) Immunoassay Reaction Procedure

The pretreated sample (about 0.9 volumes) was transferred into the well containing 1 volume of an anti-vitamin D antibody marked with alkaline phosphatase (conjugated, bioMérieux). The alkaline phosphatase antibody conjugate was diluted beforehand to about 10 μg/mL in 100 mM tris buffer of pH 7.1, 300 mM NaCl, containing human albumin. The sample/conjugate mixture was incubated in the well for about 5-7 min. Thereafter the sample/conjugate mixture was incubated in the cone for an additional 5-7 min approximately, during which competition took place between the antigen present in the sample and the vitamin D antigen fixed on the cone for sites of the antibody specific to conjugated anti-vitamin D. Thereafter, three successive washes with 200 mM tris buffer of pH 8.4, 300 mM NaCl, Tween® 20 0.2%, were performed in order to eliminate the non-fixed compound. During the final development step, the 4-methylombelliferyl phosphate substrate was sucked out and then delivered into the cone; the enzyme of the conjugate catalyzes the reaction of hydrolyzing the substrate into 4-methylombelliferyl, and the fluorescence it emits was measured at 450 nanometers (nm). The value of the fluorescence signal is inversely proportional to the concentration of the antigen present in the sample.

Table 1 below summarizes the fluorescence signals (RFV) determined by the Vidas® machine as a function of the dissociation solution used, using three different solutions of human serum. For each experimental setup, four independent measurements were made.

TABLE 1

|  | 0.75% perfluorohexanoic acid WITHOUT methanol Comparative dissociation solution | 0.75% perfluorohexanoic acid 5% methanol Solution of the invention |
|---|---|---|
| sample No. 1 at 11 ng/mL | | |
| RFV signal | 3536 | 3818 |
|  | 3457 | 3674 |
|  | 3665 | 3889 |
|  | 3356 | 3922 |
| Mean RFV | 3504 | 3826 |
| CV % | 4% | 3% |
| S/B ratio | 28.58 | 30.82 |
| sample No. 2 at 20 ng/mL | | |
| RFV signal | 2863 | 3430 |
|  | 3290 | 3189 |
|  | 3496 | 3316 |
|  | 3072 | 3149 |
| Mean RFV | 3180 | 3271 |
| CV % | 9% | 4% |
| S/B ratio | 21.32 | 28.17 |
| % ratio $RFV_{No.2}/RFV_{No.1}$ | 91% | 85% |

TABLE 1-continued

|  | 0.75% perfluorohexanoic acid WITHOUT methanol Comparative dissociation solution | 0.75% perfluorohexanoic acid 5% methanol Solution of the invention |
|---|---|---|
|  | sample No. 3 at 36 ng/mL | |
| RFV signal | 2642 | 2420 |
|  | 2440 | 2349 |
|  | 2761 | 2490 |
|  | 2815 | 2433 |
| Mean RFV | 2655 | 2423 |
| CV % | 6% | 2% |
| S/B ratio | 24.1 | 32.43 |
| % ratio $RFV_{No.3}/RFV_{No.1}$ | 76% | 63% |

It can be seen that adding alcohol improves dissociation (the signal ratio in % decreases), while improving reproducibility (increase in the signal-to-noise ratio and decrease in CV %).

EXAMPLE 2—COMPARING DIFFERENT ALCOHOLS

The dissociation solutions used in this example were prepared using the procedure explained for Example 1, in a PBS buffer with pH of 7.2. The natures and the concentrations of the fluoroalkyl surfactant and of the alcohol were varied and are set out in Tables 2 and 3.

Otherwise, the procedure was as in Example 1.

TABLE 2

| Use of perfluorohexanoic acid | | |
|---|---|---|
|  | sample No. 1 at 11 ng/mL | sample No. 2 at 35 ng/mL |
| Comparative dissociation solution: PBS + 1% perfluorohexanoic acid without alcohol | | |
| Mean RFV | 3224 | 2648 |
| % ratio $RFV_{No.2}/RFV_{No.1}$ | — | 82% |

TABLE 2-continued

| Use of perfluorohexanoic acid | | |
|---|---|---|
|  | sample No. 1 at 11 ng/mL | sample No. 2 at 35 ng/mL |
| Dissociation solution of the invention: PBS + 1% perfluorohexanoic acid + 5% methanol | | |
| Mean RFV | 3118 | 2323 |
| % ratio $RFV_{No.2}/RFV_{No.1}$ | — | 75% |
| Dissociation solution of the invention: PBS + 1% perfluorohexanoic acid + 5% ethanol | | |
| Mean RFV | 2707 | 1925 |
| % ratio $RFV_{No.2}/RFV_{No.1}$ | — | 71% |
| Dissociation solution of the invention: PBS + 1% perfluorohexanoic acid + 5% isopropanol | | |
| Mean RFV | 2633 | 2003 |
| % ratio $RFV_{No.2}/RFV_{No.1}$ | — | 76% |

It can be seen that adding alcohol, regardless of the alcohol, leads to an improvement in dissociation (the signal ratio in % decreases).

TABLE 3

| The use of perfluoroctanoic acid | | |
|---|---|---|
|  | sample No. 1 at 11 ng/mL | sample No. 2 at 35 ng/mL |
| Comparative dissociation solution: PBS + 0.75% perfluorooctanoic acid without alcohol | | |
| Mean RFV | 2684 | 1197 |
| % ratio $RFV_{No.2}/RFV_{No.1}$ | — | 45% |
| Dissociation solution: PBS + 0.75% perfluorooctanoic acid + 5% methanol | | |
| Mean RFV | 2574 | 787 |
| % ratio $RFV_{No.2}/RFV_{No.1}$ | — | 31% |
| Dissociation solution: PBS + 0.75% perfluorooctanoic acid + 5% ethanol | | |
| Mean RFV | 2612 | 759 |
| % ratio $RFV_{No.2}/RFV_{No.1}$ | — | 29% |

It can be seen that adding alcohol, regardless of the alcohol, leads to an improvement in the dissociation (signal ratio in % decreases).

EXAMPLE 3—INFLUENCE OF PERFLUOROALKYL ACID CONCENTRATION

The dissociation solutions used in this heat exchanger were prepared using the procedure explained for Example 1, in a PBS buffer with pH of 7.2.

Otherwise the procedure was as in Example 1.

TABLE 4

|  | 1.25% perfluorohexanoic acid without methanol | | 1.6% perfluorohexanoic acid without methanol | | 2% perfluorohexanoic acid without methanol | |
|---|---|---|---|---|---|---|
|  | sample No. 1 at 1 ng/mL | sample No. 2 at 35 ng/mL | sample No. 1 at 15 ng/mL | sample No. 2 at 35 ng/mL | sample No. 1 at 15 ng/mL | sample No. 2 at 35 ng/mL |
| Mean RFV | 4724 | 3844 | 4054 | 2885 | 3352 | 2252 |
| % ratio $RFV_{No.2}/RFV_{No.1}$ | — | 81% | — | 71% | — | 67% |

TABLE 4-continued

| | 1.25% perfluorohexanoic acid + 5% methanol | | 1.6% perfluorohexanoic acid + 5% methanol | | 2% perfluorohexanoic acid + 5% methanol | |
|---|---|---|---|---|---|---|
| | sample No. 1 at 15 ng/mL | sample No. 2 at 35 ng/mL | sample No. 1 at 15 ng/mL | sample No. 2 at 35 ng/mL | sample No. 1 at 15 ng/mL | sample No. 2 at 35 ng/mL |
| Mean RFV | 3896 | 2589 | 3245 | 1802 | 2564 | 1335 |
| % ratio $RFV_{No.\ 2}/RFV_{No.\ 1}$ | — | 66% | — | 56% | — | 52% |

It can be seen that the dissociation increases in the presence of alcohol under all circumstances. It can also be seen that by increasing the concentration of perfluoroalkyl acid, the dissociation is increased further.

EXAMPLE 4—INFLUENCE OF ALCOHOL CONCENTRATION

The dissociation solutions used in this example were prepared using the procedure explained for Example 1, in a PBS buffer with pH of 7.2. The natures and concentrations of the fluoroalkyl surfactant and of the alcohol were varied and they are set out in Table 5. Since ammonium perfluorooctanoate is solid, the percentages associated therewith are given by weight of ammonium perfluorooctanoate relative to the total volume of the solution.

Otherwise, the procedure was as in Example 1.

TABLE 5

| | 0.5% ammonium perfluorooctanoate without methanol | | 0.5% ammonium perfluorooctanoate + 5% methanol | | 0.5% ammonium perfluorooctanoate + 10% methanol | |
|---|---|---|---|---|---|---|
| | sample No. 1 at 15 ng/mL | sample No. 2 at 35 ng/mL | sample 1 at 15 ng/mL | sample No. 2 at 35 ng/mL | sample No. 1 at 15 ng/mL | sample No. 2 at 35 ng/mL |
| Mean RFV | 2932 | 2341 | 3944 | 2765 | 4512 | 2697 |
| CV % | 4% | 3% | 4% | 1% | 2% | 3% |
| S/B ratio | 27.37 | 29.77 | 28.62 | 38.04 | 35.85 | 29.92 |
| % ratio $RFV_{No.\ 2}/RFV_{No.\ 1}$ | — | 80% | — | 70% | — | 60% |

It can be seen that dissociation increases with increasing concentration of methanol, sometimes to the detriment of reproducibility, if the concentration is too great. The methanol concentration should therefore be adjusted by the person skilled in the art so as to find a compromise between the quantity of perfluoroalkyl surfactant and alcohol.

EXAMPLE 5—ADDING PLURONIC® F-127

The dissociation solution of the invention used in this example was prepared using the procedure explained for Example 1, in a 50 mM Tris buffer with pH of 7.5, with the exception that the fluoroalkyl surfactant was 1.5% perfluorohexaonic acid and the alcohol was 5% methanol. The Pluronic® F-127 was used at a concentration of 0.25%, or else none was used. The results are given in Table 6 below.

Otherwise the procedure was as in Example 1.

TABLE 6

| | Without Pluronic F-127 Mean RFV CV % | 0.25% Pluronic F-127 Mean RFV CV % |
|---|---|---|
| 0 ng/mL point | 5388 1% | 5155.5 0% |
| 11 ng/mL point | 3593 5% | 3722 2% |
| 19 ng/mL point | 2693 3% | 3063 2% |
| 30 ng/mL point | 1492 3% | 2024 0% |
| 102 ng/mL point | 295 6% | 413 2% |

TABLE 6-continued

| | Without Pluronic F-127 Mean RFV CV % | 0.25% Pluronic F-127 Mean RFV CV % |
|---|---|---|
| sample No. 1 | 1069 3% | 1597 2% |
| sample No. 2 | 2179 4% | 2914 2% |
| sample No. 3 | 188 1% | 401 1% |
| sample No. 4 | 625 6% | 1328 2% |

Adding an additional surfactant such as Pluronic® F-127 serves to improve reproducibility (reduction in CV %). The improvement in reproducibility is greater for samples having a high concentration of vitamin D.

EXAMPLE 6—INFLUENCE OF THE BUFFER USED

The comparative dissociation solution and the dissociation solution of the invention with the mention PBS as used in this example were prepared using the procedure explained for Example 1 in a PBS buffer with pH of 7.2. The natures and the concentrations of the fluoroalkyl surfactant and of the alcohol, if any, are given in Table 7 (comparative solution) and in Table 9 (solution of the invention).

The comparative dissociation solution and the dissociation solution of the invention bearing the mention Tris contained 50 mM of Tris, the fluoroalkyl surfactant, with or without alcohol. The components were dissolved in demineralized water by stirring for about 30 min. The pH was adjusted to 7.5 with 6N NaOH. The natures and the concentrations of the fluoroalkyl surfactant and of the alcohol, if any, are given in Table 8 (comparative solution) and in Table 9 (solution of the invention).

TABLE 7

Comparative dissociation solution: PBS + 1.5% perfluorohexanoic acid

|  | sample No. 1 at 11 ng/mL | sample No. 2 at 30 ng/mL |
|---|---|---|
| Mean RFV | 2510 | 1509 |
| % ratio $RFV_{No.2}/RFV_{No.1}$ | — | 60% |

TABLE 8

Comparative dissociation solution: Tris + 1.5% perfluorohexanoic acid

|  | sample No. 1 at 11 ng/mL | sample No. 2 at 30 ng/mL |
|---|---|---|
| Mean RFV | 2779 | 1618 |
| % ratio $RFV_{No.2}/RFV_{No.1}$ | — | 58% |

TABLE 9

Dissociation solution of the invention: PBS buffer or Tris buffer + 1.5% perfluorohexanoic acid + 5% methanol

|  | sample No. 1 at 11 ng/mL | | sample No. 2 at 30 ng/mL | |
|---|---|---|---|---|
| Buffer | PBS | TRIS | PBS | TRIS |
| Mean RFV | 4181 | 4874 | 1665 | 2030 |
| % ratio $RFV_{No.2}/RFV_{No.1}$ | — | — | 40% | 42% |

It can be seen that the nature of the buffer has no significant influence on the RFV ratio, and thus on the resulting dissociation.

The sole FIGURE plots the B/B0% ratio obtained over an ng/mL range of analyte for both buffers (PBS buffer and Tris buffer). The B/B0% ratio is the signal obtained for the range point under test divided by the signal obtained for the range point having 0 ng/ml, of analyte, multiplied by 100.

It can be seen that the choice of buffer used has no significant influence on the results obtained, whether in terms of dissociation or in terms of reproducibility.

The invention claimed is:

1. A buffer solution comprising methanol and at least one fluoroalkyl surfactant selected from the group consisting of perfluorohexanoic acid, perfluoroheptanoic acid, and perfluorooctanoic acid and their salts, which comprises a percentage by volume of methanol relative to the total volume of the solution lying in the range 2% to 10%, and a percentage of fluoroalkyl surfactant by volume when the fluoroalkyl surfactant is liquid, or by weight when the fluoroalkyl surfactant is solid, relative to the total volume of the solution, lying in the range of 0.1% to 3%.

2. A buffer solution according to claim 1, characterized in that it comprises a percentage of fluoroalkyl surfactant by volume when the surfactant is liquid, or by weight when it is solid, relative to the total volume of the solution lying in the range 1% to 2%.

3. A buffer solution according to claim 1, characterized in that it comprises a percentage by volume of methanol relative to the total volume of the solution lying in the range 2% to 7%.

4. A buffer solution according to claim 1, characterized in that the fluoroalkyl surfactant and the methanol are present in quantities such that the ratio multiplied by 100 of the weight of surfactant, when it is solid, or of the volume of surfactant, when it is liquid, over the volume of methanol lies in the range 10% to 60%.

5. A buffer solution according to claim 1, characterized in that the fluoroalkyl surfactant and the methanol are present in quantities such that the ratio multiplied by 100 of the weight of surfactant, when it is solid, or of the volume of surfactant, when it is liquid, over the volume of methanol lies in the range in the range 15% to 30%.

6. A buffer solution according to claim 1, characterized in that it contains perfluorohexanoic acid and methanol.

7. A buffer solution according to claim 1, characterized in that it further contains an additional surfactant selected from block copolymers based on ethylene oxide and propylene oxide, polysorbates, and polyethylene glycol ethers.

8. A buffer solution according to claim 1, characterized in that it is buffered to a pH lying in the range 6 to 8.

9. A buffer solution according to claim 1, characterized in that it does not contain any of the following compounds: dimethyl sulfoxide, dimethylformamide, N,N-dimethylacetamide, tetramethylurea, N-methylpyrrolidone, 1,3-dimethyl-3,4,5,6-tetrahydro-2(1H)-pyrimidone, triamide hexamethyl phosphoric acid.

10. A detection and quantification method for detecting and quantifying, in vitro, vitamin D and/or at least one vitamin D metabolite in a biological sample, the method comprising the following steps:
    a) a step of mixing the sample with the buffer solution according to claim 1, so as to dissociate the vitamin D and/or its metabolite(s) to be detected from vitamin D binding protein; and
    b) a step of detecting and quantifying vitamin D and/or at least one of its metabolites.

11. The detection and quantification method according to claim 10, characterized in that 1 to 20 volumes of the buffer solution are used for 1 volume of sample.

12. The detection and quantification method according to claim 10, characterized in that the biological sample is a sample of blood, of serum, or of plasma.

13. The detection and quantification method according to claim 10, characterized in that in step b), 25-hydroxy vitamin $D_2$ and/or 25-hydroxy vitamin $D_3$ is/are detected.

14. The detection and quantification kit for detecting vitamin D and/or at least one vitamin D metabolite by immunoassay, the kit comprising the buffer solution according to claim 1 and a binding partner for vitamin D or one of its metabolites.

15. The detection and quantification kit according to claim 14, characterized in that the binding partner is a marked antibody and the kit further comprises a solid phase on which there is bonded a hapten analogous to vitamin D and/or to the vitamin D metabolite(s) for detection, which hapten is recognized by the marked antibody.

* * * * *